United States Patent [19]

Lai et al.

[11] Patent Number: 5,352,714
[45] Date of Patent: Oct. 4, 1994

[54] WETTABLE SILICONE HYDROGEL COMPOSITIONS AND METHODS FOR THEIR MANUFACTURE

[75] Inventors: Yu-Chin Lai, Pittsford; Gary D. Friends, Ontario; Paul L. Valint, Jr., Pittsford, all of N.Y.

[73] Assignee: Bausch & Lomb Incorporated, Rochester, N.Y.

[21] Appl. No.: 922,594

[22] Filed: Jul. 30, 1992

Related U.S. Application Data

[63] Continuation-in-part of Ser. No. 788,067, Nov. 5, 1991, abandoned.

[51] Int. Cl.⁵ .................. C08F 230/08; C08F 26/06; C08F 30/08
[52] U.S. Cl. .................. 523/107; 526/260; 526/279; 524/95; 524/96; 524/97
[58] Field of Search ............. 523/107; 526/279, 260; 524/95–97

[56] References Cited

U.S. PATENT DOCUMENTS

| | | | |
|---|---|---|---|
| 4,120,570 | 10/1978 | Gaylord | 351/40 |
| 4,123,408 | 10/1978 | Gordon | 260/29.6 |
| 4,136,250 | 1/1979 | Mueller | 528/29 |
| 4,192,827 | 3/1980 | Mueller | 525/123 |
| 4,216,303 | 8/1980 | Novicky | 528/32 |
| 4,277,582 | 7/1981 | Mueller | 525/421 |
| 4,279,795 | 7/1981 | Yamashita | 260/29.6 |
| 4,314,068 | 2/1982 | Novicky | 556/440 |
| 4,348,329 | 9/1982 | Chapman | 260/403 |
| 4,355,147 | 10/1982 | Deichert | 526/264 |
| 4,535,138 | 8/1985 | Ratkowski | 526/279 |
| 4,605,712 | 8/1986 | Mueller | 525/474 |
| 4,666,249 | 5/1987 | Bauman | 351/160 |
| 4,687,816 | 8/1987 | Lin | 525/279 |
| 4,740,533 | 4/1988 | Su | 523/106 |
| 4,786,657 | 11/1988 | Hammar | 522/90 |
| 4,810,764 | 3/1989 | Friends | 526/245 |
| 4,886,866 | 12/1989 | Braatz | 528/59 |
| 4,904,421 | 2/1990 | Ando | 264/2.6 |
| 4,910,277 | 3/1990 | Bambury et al. | 526/260 |
| 4,925,698 | 5/1990 | Klausner | 427/2 |
| 4,959,074 | 9/1990 | Halpern | 623/66 |
| 4,961,954 | 10/1990 | Goldberg | 427/2 |
| 5,034,461 | 7/1991 | Lai et al. | 525/100 |

FOREIGN PATENT DOCUMENTS 0328340  8/1989  European Pat. Off. ............. 230/08

Primary Examiner—Paul R. Michl
Assistant Examiner—La Vonda DeWitt
Attorney, Agent, or Firm—David M. Krasnow; Craig E. Larson

[57] ABSTRACT

Improved silicone-containing hydrogels are disclosed with enhanced wettability comprising a silicone-containing monomer, hydrophilic monomers, and a relatively non-polar ring-containing monomer able to be converted to a highly polar amino acid upon hydration.

23 Claims, No Drawings

WETTABLE SILICONE HYDROGEL COMPOSITIONS AND METHODS FOR THEIR MANUFACTURE

BACKGROUND OF THE INVENTION

This application is a continuation-in-part application of copending application Ser. No. 07/788,067 filed Nov. 5, 1991, which is now abandoned.

FIELD OF THE INVENTION

The present invention relates to improved wettable polymeric hydrogel compositions useful for the production of biomedical devices, especially contact lenses.

BACKGROUND

Hydrogels have been a desirable class of material for the preparation of biomedical devices, and have been known since at least Wichterle, et al U.S. Pat. No. 3,220,960 which disclosed hydrogels comprising a hydrated polymer of a hydroxyalkyl acrylate or methacrylate crosslinked with a corresponding diester poly (2-hydroxyethyl methacrylate), known as poly-HEMA.

A hydrogel is a hydrated crosslinked polymeric system that contains water in an equilibrium state. The physical properties of hydrogels can vary widely and are mostly determined by their water content. Since hydrogels exhibit excellent biocompatibility, there has been extensive interest in the use of hydrogels for biomedical devices, especially contact lenses.

In the field of contact lenses, various factors combine to yield a material that has appropriate characteristics. Oxygen permeability, wettability, material strength and stability are but a few of the factors which must be carefully balanced to achieve a useable end-result contact lens. Since the cornea receives its oxygen supply exclusively from contact with the atmosphere, good oxygen permeability is a critical characteristic for any contact lens material.

It was discovered in the field that certain crosslinked polymeric materials could be hydrated and retain their water content. It was further found that the higher the water content within contact lenses made from these crosslinked hydrogel polymers, the greater was the oxygen permeability through the lens to the eye and its cornea.

High water-containing hydrogels have at times exhibited undesirable mechanical properties. For example, such hydrogels are often not easily formed into hydrolytically stable lenses. Further such materials have at times exhibited tearing or other breakage as a result of poor tensile strength. What was needed was a highly oxygen permeable material that was durable and highly wettable. Wettability is important in that if the lens is not sufficiently wettable, it does not remain lubricated and therefore cannot be worn comfortably in the eye. The optimal contact lens would have not only excellent oxygen permeability but also excellent tear fluid wettability.

Silicone-containing materials were tried as viable contact lens materials and displayed very good oxygen permeability and durability. Most silicone-containing materials are largely hydrophobic and therefore not sufficiently wettable. Wettability is important, in that, if the lens is not wettable it does not remain lubricated and therefore cannot be comfortably worn in the eye. The optimum contact lens material would have not only excellent oxygen permeability, but also excellent tear fluid wettability.

Further, it is believed that the hydrophobicity generally accompanying silicone-containing material may cause deposit problems, which may result in discomfort when wearing contact lenses made from these silicone-containing polymers.

Therefore, an optimal hydrogel material for biomedical devices, such as contact lenses, would have ideal rigidity, high oxygen permeability and a high degree of wettability.

SUMMARY OF THE INVENTION

The surface wettability of hydrogels such as silicone-containing hydrogels, and more specifically polyurethane-silicone hydrogels and ethylenically terminated poly(organosiloxane) hydrogels, can be significantly enhanced by incorporating, as a wetting agent, at least one relatively non-polar ring-containing monomer able to be converted to a highly polar amino acid-containing monomer upon hydrolysis, or a (meth)acrylamido alkanoic acid derivative, into the silicone-containing hydrogel composition.

In accordance with this invention, a method for making a silicone-containing hydrogel composition is disclosed comprising the steps of a) combining at least one relatively non-polar ring-containing monomer able to be converted to a highly polar amino acid upon hydration with at least one silicone-containing prepolymer into a monomer mix and b) curing the monomer mix resulting from step a) to form a silicone-containing hydrogel composition.

In further accordance with the invention a method for making a silicone-containing hydrogel composition comprising the steps of a) combining at least one (meth)acrylamido alkanoic acid with at least one silicone-containing prepolymer into a monomer mix and b) curing the monomer mix resulting from step a) to form a silicone-containing hydrogel composition.

It is believed that these wetting agents react with the predominantly hydrophobic silicone-containing monomers to produce highly wettable hydrogels.

DETAILED DESCRIPTION OF THE INVENTION

The present invention relates to improved wettability of hydrogels, especially silicone-containing hydrogels, such as urethane-containing hydrogels having ideal rigidity suitable for biomedical applications such as contact lenses.

The wetting agents of the present invention enhance wettability through their incorporation into the resulting silicone-containing hydrogel compositions. The wetting agents are further characterized as relatively non-polar ring-containing monomers able to be converted to highly polar amino acids upon hydration. The wetting agent may also be a (meth)acrylamido alkanoic acid derivative, or the linear forms of the above-mentioned ring-containing monomers that occur upon hydration. One preferred class of ring-containing monomers contemplated by the present invention are the ring-containing oxazolones of the general formula:

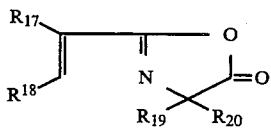

where

R$_{17}$ and R$_{18}$ independently denote H or CH$_3$; and

R$_{19}$ and R$_{20}$ independently denote methyl or cyclohexyl radicals.

These preferred ring-containing wetting agents include 2-isopropenyl-4,4-dimethyl-2-oxazolin-5-one (IPDMO), 2-vinyl-4,4-dimethyl-2-oxazolin-5-one (VDMO), cyclohexane spiro-4'-(2'isopropenyl-2'-oxazol-5'-one) (IPCO), cyclohexane-spiro-4'-(2'-vinyl-2'-oxazol-5'-one) (VCO), and 2-(-1-propenyl)-4,4-dimethyl-oxazol-5-one (PDMO), with VDMO being the most preferred. The preferred oxazolones are prepared by known reaction sequences set forth in commonly assigned U.S. Pat. No. 4,810,764.

It was found that these hydrophilic monomers having a ringed structure, such as 2-vinyl-4,4-dimethyl-2-oxazalin-5-one, or VDMO, can copolymerize well with any (meth)acrylate and (meth)acrylamide monomer or prepolymer to form a hydrophilic copolymer or hydrogel. The prepolymerized VDMO can hydrolyze in water, thereby breaking the ringed structure to form the corresponding polar acid which becomes ionic after being placed in buffered saline solution (pH 7.4). A "prepolymer" is a polymer of medium molecular weight having polymerizable groups.

Further notations such as "(meth)acrylate" or "(meth)acrylamide" are used herein to denote optional methyl substitution. Thus, for example, methyl (meth)acrylate includes both methyl acrylate and methyl methacrylate and N-alkyl (meth)acrylamide includes both N-alkyl acrylamide and N-alkyl methacrylamide.

It is further contemplated by the present invention that the straight chain acid equivalents to the opened ring structure, or (meth)acrylamide alkanoic acid-containing monomer could be added to the hydrogel mix in the linear form in the first instance. However, the enhanced solubility of the ring-containing structures in a hydrogel formulation containing the predominantly non-polar silicone monomers make the use of the ringed structures more desirable over their corresponding acids and other acid-containing (meth)acrylamides.

Further, these preferred wetting agents have at least two important features which make them particularly desirable wetting agents: (1) they are relatively non-polar and are compatible with the hydrophobic monomers (the polysiloxanes and the toughening agents), and (2) they are converted upon mild hydrolysis and change from their ringed structure to become highly polar amino acids which impart substantial wetting characteristics. When polymerized in the presence of the other components, a copolymer is formed. These wetting agents result through the carbon-carbon double bond with the endcaps of the polysiloxane monomers, and with the toughening agents used in polymeric syntheses and known to those skilled in the art, to form copolymeric materials particularly useful in biomedical devices, especially contact lenses.

The preferred range of the wetting agent concentration is from about 0.5 weight percent of the polymeric mix to about 10 weight percent, and more preferably from about 1 weight percent to about 5 weight percent.

Silicone hydrogels (i.e., hydrogels containing silicone) are usually prepared by polymerizing a mixture containing at least one silicone-containing monomer and at least one hydrophilic monomer. Either the silicone-containing containing monomer or the hydrophilic monomer may function as a crosslinking agent (a crosslinker being defined as a monomer having multiple polymerizable functionalities) or a separate crosslinker may be employed.

Any known silicone-containing monomer may be used in the process of this invention to form the silicone hydrogels of this invention, as will be apparent to one skilled in the art. The monomers added to the monomer mix to create the monomeric mixture may be monomers or prepolymers. A "prepolymer" is a reaction intermediate polymer of medium molecular weight having polymerizable groups. Thus it is understood that the terms "silicone-containing monomers" and "hydrophilic monomers" include prepolymers. Examples of such monomers may be found in U.S. Pat. Nos. 4,136,250; 4,153,641; 4,740,533; 5,034,461; and 5,070,215.

Additional crosslinking agents which may be incorporated into the silicone-containing hydrogel of the present invention include polyvinyl, typically di- or tri-vinyl monomers, most commonly the di- or tri(meth)acrylates of dihydric ethylene glycol, triethylene glycol, butylene glycol, hexane-1,6-diol, thio-diethylene glycol-diacrylate and methacrylate; neopentyl glycol diacrylate; trimethylolpropane triacrylate and the like; N,N'-dihydroxyethylenebisacrylamide and -bismethacrylamides; also diallyl compounds like diallyl phthalate and triallyl cyanurate; divinylbenzene; ethylene glycol divinyl ether; and the (meth)acrylate esters of polyols such as triethanolamine, glycerol, pentanerythritol, butylene glycol, mannitol, and sorbitol. Further, illustrations include N,N-methylene-bis-(meth)acrylamide, sulfonated divinylbenzene, and divinylsulfone. Also useful are the reaction products of hydroxyalkyl (meth)acrylates with unsaturated isocyanates, for example the reaction product of 2-hydroxyethyl methacrylate with 2-isocyanatoethyl methacrylate (IEM) as disclosed in U.S. Pat. No. 4,954,587.

Other known crosslinking agents are polyetherbisurethane-dimethacrylates as described in U.S. Pat. No. 4,192,827, and those crosslinkers obtained by reaction of polyethylene glycol, polypropylene glycol and polytetramethylene glycol with 2-isocyanatoethyl methacrylate (IEM) or m-isopropenyl-$\gamma$, $\gamma$, -dimethylbenzyl isocyanates (m-TMI), and polysiloxane-bisurethane-dimethacrylates as described in U.S. Pat. Nos. 4,486,577 and 4,605,712. Still other known crosslinking agents are the reaction products of polyvinyl alcohol, ethoxylated polyvinyl alcohol or of polyvinyl alcohol-co-ethylene with 0.1 to 10 mol % vinyl isocyanates like IEM or m-TMI.

One preferred class of suitable silicone-containing prepolymers contemplated by the present invention are bulky polysiloxanylalkyl (meth)acrylic monomers represented by the formula (I):

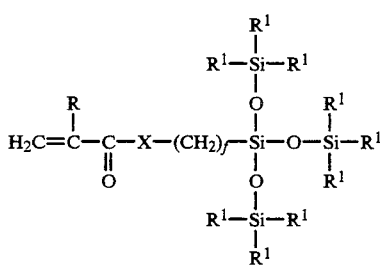

wherein:

X is O or NR;

each R is independently hydrogen or methyl; and each $R^1$ is independently a lower alkyl or phenyl group; and f is 1 or 3 to 10.

Such bulky monomers include methacryloxypropyl tris(trimethylsiloxy)silane, pentamethyldisiloxanylmethylmethacrylate, tris(trimethylsiloxy)methacryloxy propylsilane, phenyltetramethyldisiloxanylethyl acetate, and methyldi(trimethylsiloxy)methacryloxymethyl silane.

A further preferred class of silicone-containing prepolymers is a poly(organosiloxane) prepolymer represented by the formula (II):

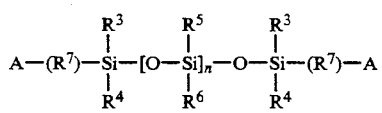

wherein:

A is an activated unsaturated group, such as an ester or amide of an acrylic or a methacrylic acid;

each $R^3$-$R^6$ is independently selected from the group consisting of a monovalent hydrocarbon radical or a halogen substituted monovalent hydrocarbon radical having 1 to 18 carbon atoms which may have ether linkages between carbon atoms;

$R^7$ is a divalent hydrocarbon radical having from 1 to 22 carbon atoms; and n is O or an integer greater than or equal to 1.

A further preferred class of silicone-containing prepolymers are those monomers having the following schematic representations:

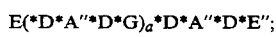

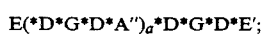

where

D denotes an alkyl diradical, an alkyl cycloalkyl diradical, a cycloalkyl diradical, an aryl diradical or an alkylaryl diradical having 6 to 30 carbon atoms;

G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

a is at least 1;

A'' denotes a divalent polymeric radical of formula (V):

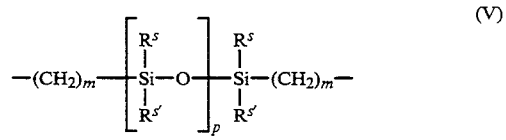

wherein:

$R^s$ and $R^{s'}$ independently denote an alkyl or fluoro-substituted alkyl group having 1 to 10 carbon atoms which may contain ether linkages between carbon atoms;

m is at least 1; and p provides a moiety weight of 400 to 10,000;

E and E' independently denote a polymerizable unsaturated organic radical represented by formula (VI):

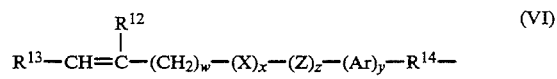

wherein: $R^{14}$ denotes a divalent alkylene radical having 1 to 10 carbon atoms;

$R^{12}$ denotes H or $CH_3$;

$R^{13}$ denotes H, a ($C_1$-$C_6$) alkyl radical or a —CO—Y—$R^{15}$ group wherein Y is —O—, —S— or —NH— and $R^{15}$ is a alkyl radical having 1 to 12 carbon atoms;

X is —CO— or —OCO—;

Z is —O— or —NH—;

Ar denotes an aromatic radical having 6 to 30 carbon atoms;

w is 0 to 6;

x is 0 or 1;

y is 0 or 1; and z is 0 or 1.

A preferred urethane prepolymer is represented by formula (VII):

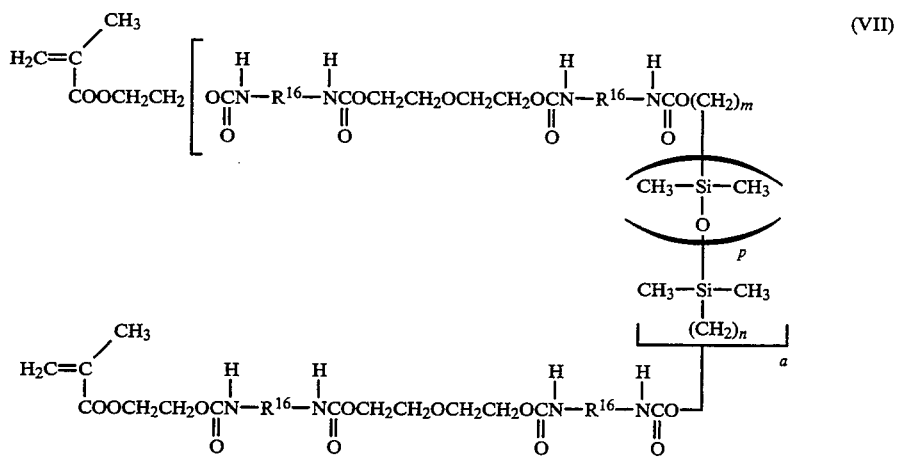

(VII)

wherein:

$R^{16}$ is a diradical of a diisocyanate after removal of the isocyanate group, and is most preferably the diradical of isophorone diisocyanate, and m, p and a are the same as previously defined. Preferably, the sum of m and a is 3 or 4, and more preferably, a is 1 and m is 3 or 4. Preferably, p is at least 30.

The monomer mixes employed in this invention, can be readily cured to cast shapes by conventional methods such as UV polymerization, or thermal polymerization, or combinations thereof, as commonly used in polymerizing ethylenically unsaturated compounds. Representative free radical thermal polymerization initiators are organic peroxides, such as acetal peroxide, lauroyl peroxide, decanoyl peroxide, stearoyl peroxide, benzoyl peroxide. tertiarybutyl peroxypivalate, peroxydicarbonate, and the like, employed in a concentration of about 0.01 to 1 percent by weight of the total monomer mixture. Representative UV initiators are those known in the field such as, benzoin methyl ether, benzoin ethyl ether, Darocure 1173, 1164, 2273, 1116, 2959, 3331 (EM Industries) and Igracure 651 and 184 (Ciba-Geigy).

Polymerization of the monomer mix of this invention may be performed in the presence of a diluent. The polymerization product will then be in the form of a gel. If the diluent is nonaqueous, the diluent must be removed from the gel and replaced with water through the use of extraction and hydration protocols well known to those skilled in the art.

It is also possible to perform the polymerization in the absence of diluent to produce a xerogel. These xerogels may then be hydrated to form the hydrogels as is well known in the art.

In addition to the above-mentioned polymerization initiators, the copolymer of the present invention may also include other monomers as will be apparent to one skilled in the art. For example, the monomer mix may include additional hydrophilic monomers such as N-vinyl pyrrolidone and N,N-dimethyl acrylamide, colorants, or UV-absorbing and toughening agents such as those known to those skilled in the contact lens art.

The polymers of this invention can be formed into contact lenses by spincasting processes (such as those disclosed in U.S. Pat. Nos. 3,408,429 and 3,496,254), cast molding (such as those disclosed in U.S. Pat. Nos. 4,084,459 and 4,197,266), combinations of methods thereof, or any other known method for making contact lenses. Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates or rods, which may then be processed (e.g., cut or polished via lathe or laser) to give a contact lens having a desired shape.

It is contemplated that the wettable silicone-containing hydrogels of the present invention, when used in contact lens applications, can produce a wide variety of types of hydrogel contact lenses. As is understood in the field, in general, hydrogel contact lenses should have oxygen permeabilities with DK values greater than $20 \times 10^{-11}$ cm$^3$ × cm/sec × cm$^2$ × mmHg (or DK units) and preferably greater than 60 DK. They should have a Young's modulus of elasticity in the range of 5 to 400 g/mm$^2$, preferably greater than 20g/mm$^2$ as measured by ASTM test method D1938. Their water content should be between 10 to 80%, and preferably between 20 to 60%. The contact angle, which is a measurement of the wettability of the lens, should be less than 80 degrees and should preferably be less than 40 degrees.

The present invention further provides articles of manufacture which can be used for biomedical devices, such as, contact lenses, surgical devices, heart valves, vessel substitutes, intrauterine devices, membranes and other films, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, denture liners, intraocular devices, and especially contact lenses. It is known that blood, for example, is readily and rapidly damaged when it comes into contact with artificial surfaces. The design of a synthetic surface which is antithrombogenic and non-hemolytic to blood is necessary for prostheses and devices used with blood.

The terms "shaped articles for use in biomedical applications" or "biomedical devices" mean the materials disclosed herein have physicochemical properties rendering them suitable for prolonged contact with living tissue, blood and the mucous membranes.

Although the exact mechanisms are not fully understood at the present time, the wetting agents of the present invention appear to reduce the deposition problems normally associated with, and believed to be caused by, the high hydrophobicity of the hydrophobic silicone-containing prepolymers.

Further, the wetting agents of the present invention significantly reduce the contact angle of the surface—a clear indication to those skilled in the field that enhanced wetting has occurred. The resulting hydrogels comprising the wetting agents of the present invention were unexpectedly hydrolytically stable, within an acceptable range, while collecting only an acceptable level of deposits.

Two preferred classes of silicone-containing monomers contemplated by the present invention are urethane-containing prepolymers, and ethylenically terminated polysiloxane-containing monomers as previously described herein, such as, preferably α, ω bis(methacryloxyalkyl)polysiloxane ($M_2D_x$).

The resulting polymers and copolymers disclosed herein can be boiled and/or autoclaved in water without being damaged whereby sterilization may be achieved. Thus, an article formed from the disclosed polymers and copolymers may be used, for example, in surgery where an article is needed which is compatible with living tissue or with the mucous membranes.

The following examples serve only to further illustrate aspects of the present invention and should not be construed as limiting the invention.

The following abbreviations are defined as follows:
NVP is N-vinyl pyrrolidone
DMA is N,N-dimethylacrylamide
HEMAVc is methacryloxyethyl vinyl carbonate
TRIS is methacryloxypropyltris (trimethylsiloxy)silane
IDS3H is a urethane prepolymer derived from isophorone diisocyante diethylene glycol polysiloxanediol and end-capped with 2-hydroxyethyl methacrylate
$M_2D_x$ is an α, ω, -bis(methacryloxyalkyl)polysiloxane
VDMO is 2-vinyl-4,4-dimethyl-2-oxazoline-5-one

EXAMPLE 1

Preparation of Polyurethane Monomer Mix (Control)

A formulation containing the following was prepared: IDS3H, diethylene glycol, polysiloxanediol of molecular weight 3000 and HEMA, 35 parts; TRIS, 35 parts; DMA, 30 parts; n-hexanol, 40 parts; BME, 0.2 part. The resulting clear mix was then UV cured into films between two silane-treated glass plates or filtered through a 1.2 micron filter into a clean glass vial ready for lens casting.

EXAMPLE 2

Preparation of Polyurethane Monomer Mix with 2-vinyl-4,4-dimethyl-2-oxazolin-5-one (VDMO)

A polyurethane monomer mix was prepared as in Example 1 except that 5 parts of VDMO was added. The monomer mix was cured in the same fashion as in Example 1.

EXAMPLE 3

Preparation of Polyurethane Monomer Mix with Methacrylic Acid

A polyurethane monomer mix was prepared as in Example 1, except 2 parts of methacrylic acid (MAA) was added to the mix. The monomer mix was cured under UV conditions into films as described in Example 1.

EXAMPLE 4

Polyurethane Formulation with VDMO/NVP

A polyurethane formulation containing the same urethane prepolymer as in Example 1, 30 parts; TRIS, 30 parts; NVP, 27 parts; DMA, 9 parts; VDMO, 1 part; methacryloxyethyl vinyl carbonate (HEMAVc), 0.1 part; Darocur-1173, 0.2 part; and hexanol 40 parts, was prepared and cast into films as done in Examples 1–3 and processed in the same fashion.

EXAMPLE 5

Polyurethane Hydrogel Films Properties

The formulations of Examples 1–4 were extracted with ethanol for 16 hours, boiled in water for 4 hours, and then placed in a phosphate buffered saline solution (pH 7.4). The water content and extractibles were measured for the films gravimetrically. The tensile strength and tear properties were determined according to the standard ASTM procedures 1708 and 1938 respectively. The oxygen permeabilities were determined by polarographic method with the consideration of edge effect. See (Fatt, Rasson and Melpolder, International Contact Lens Clinic 14, 389 (1987)). The properties measured from the resultant hydrogel films derived from compositions listed in Examples 1–4 are tabulated below.

|  | Formulations | | | |
| --- | --- | --- | --- | --- |
| Properties | Control | VDMO | MAA | VDMO + NVP |
| % Extractables | 5.5 | 6.3 | 6.7 | 5.5 |
| % Water Content | 23 | 39 | 35 | 40 |
| O₂ Permeability (Dk) | 110 | 70 | 79 | 90 |
| Tensile Modulus (g/mm²) | 100 | 130 | 130 | 110 |
| Tear (g/mm) | 15 | 6 | 7 | 8 |

EXAMPLE 6

Hydrolytic Stability Testing of Polyurethane Hydrogel Films

The cured films, after being extracted with solvent and dried in vacuo, were cut into disks with a 250 micron thickness and weighing 30 mg each. They were weighed while dry and were submerged into buffered saline (pH 7.4) in 12 vials and sealed. After equilibration, the films were placed in an oven at 80 degrees C. Three vials were taken out after 3, 5, 7, and 14 days. The dry weight and the water content was determined gravimetrically. The hydrolytic stabilities were reported as % weight loss over 14 days. Experimentally, it was determined that resultant hydrogels with a weight loss of 7% or less would be considered stable. The amount of VDMO and MAA present were comparable on a molar basis. The water weight loss and water content for the hydrogel films are listed below for comparison.

|  | Formulation | | |
| --- | --- | --- | --- |
| Properties | Control | VDMO | MAA |
| Weight Loss (%) | 1.3 | 6.5 | 11.5 |
| Water Content (%) | 23 | 40 | 43 |

EXAMPLE 7

Contact Angle/Wettability

The contact angles of the surface of the films prepared in Examples 1–3 were measured by the captive bubble method. The films were submerged in buffered saline solution and a bubble of air was measured using a goinometer. The contact angles based on cast lenses were also measured similarly. A lower contact angle represents a greater degree of hydrophilicity or film surface wettability. The contact angles of the controlled hydrogel films and the films modified with 5 parts VDMO and 2 parts MAA were compared.

| Contact Angle | Formulations | | |
| --- | --- | --- | --- |
| | Control | VDMO | MAA |
| Films | 38 | 22 | 22 |
| Lenses | 34 | 19 | 14 |

EXAMPLE 8

Lysozyme Uptake

The tests were accomplished by agitating hydrogel films of known weight, usually about 30–40 mg, in a vial containing standard buffered saline with 500 ppm of lysozyme for a seven day period. The amount of lysozyme remaining in the solution was determined by UV spectroscopy and the lysozyme uptake was reported as micrograms of lysozyme per mg of hydrogel film. Poly(2-hydroxyethyl methacrylate) hydrogel films were used as reference during the test. The lysozyme uptakes of the hydrogels tested were measured.

| | Formulation | | |
| --- | --- | --- | --- |
| | Control | VDMO | MAA |
| Lysozyme Uptake (ug/mg) | 5 | 14 | 24 |

EXAMPLE 9

Preparation of $M_2D_{25}$ Monomer Mix (Control)

An $\alpha,\omega$-Bis(methacryloxybutyl)polysiloxane ($M_2D_{25}$) was prepared from the reaction of 1,3-Bis(4-methacryloxybutyl)disiloxane and 1,1,3,3,5,5-hexamethyl trisiloxane in molar ratio of 1:8.33. The $M_2D_{25}$ was combined with TRIS, 47 parts; DMA, 40 parts; and Darocur-1173 (EM Industries), 0.2 parts. The mix was UV cured into films between two glass plates.

EXAMPLE 10

Preparation of $M_2D_{25}$ Monomer Mix Containing VDMO

A $M_2D_{25}$ monomer mix was prepared as described in Example 8 except that 1 part VDMO was added. The monomer mix was cured as described in Example 1.

EXAMPLE 11

Hydrogel Film properties for Formulations Containing $M_2D_{25}$

The processing and tests of these films were performed in the same manner as described in Example 4.

| Properties | Formulation | |
| --- | --- | --- |
| | Control | VDMO |
| % Extractable | 1.0 | 1.5 |
| Water Content | 29 | 32 |
| $O_2$ Permeability (Dk) | 98 | 90 |
| Tensile Modulus (g/mm$^2$) | 89 | 96 |
| % Elongation | 156 | 140 |
| Tear g/mm | 12 | 9 |

EXAMPLE 12

Hydrolytic Stability of $M_2D_{25}$ Hydrogel Films

The tests were performed as described in Example 4. The results are listed below.

| Formulation | Example 9 | Example 10 |
| --- | --- | --- |
| Wt. Loss (%) | 1.5 | 5.7 |
| Water Content | 30 | 32 |

EXAMPLE 13

Lens Fabrication

A polyurethane mix of the formulation as described in Example 1 was filtered through 1.2 micron millipore disposable filter into a clean vial. Under an inert nitrogen atmosphere, 60–90 ul of the mix was injected onto a clean plastic mold half and then covered with a second plastic mold half. The molds were then compressed and cured for 90 minutes in the presence of UV light (4200 microwatts/cm$^2$). The molds were then opened mechanically and put into a beaker containing aqueous ethanol. The lenses were released from the molds within 1 hour, then extracted with ethanol for 48 hours, and boiled in distilled water for 4 hours. The resultant lenses were inspected for cosmetic quality and dimension. Lenses passing inspection were thermally disinfected in phosphate buffered saline prior to on-eye evaluation.

The polyurethane containing VDMO of Examples 2 and 4, and the $M_2D_{25}$ formulations were cast and processed in exactly the same manner as outlined immediately above.

EXAMPLE 14

Clinical Evaluations

The cast-molded polyurethane lenses described in Example 12 were evaluated on six to ten patients. In each test, a poly(HEMA) control lens was worn on one eye and the test lens on the other eye. The lenses were analyzed after a minimum of one hour, and preferably 5 hours or longer for wettability and surface deposition study. The surface wettability rating scale was 0–4 with 0 representing ⅔ of the anterior surface unwetted by the tear film, and 4 representing complete wetting. The deposition scale was also 0–4 with 0 representing no surface deposit and 4 representing multiple deposits of 0.5 mm diameter or larger. The results for the lenses of the control formulation (according to Example 1) was 2.0 for wetting and 1.6 for deposit after one hour of wear. For lenses comprising 5 parts of VDMO (Example 2 formulation), the results showed a wettability rating of 3.3 and a deposit rating of 0.3 after 6 hours or wear. This indicated that the VDMO-containing lenses have superior wettability and deposit resistance characteristics resulting in a much higher rate of acceptance.

Many other modifications and variations of the present invention are possible to the skilled practitioner in the field in light of the teachings herein. It is therefore understood that, within the scope of the claims, the present invention can be practiced other than as herein specifically described.

We claim:

1. A method for making a silicone-containing hydrogel composition comprising the steps of a) combining a ring-containing oxazolone monomer in the amount of from about 0.5 to about 10 weight percent able to be converted to a highly polar hydrophilic amino acid upon hydration with an α, ω-bis(methacryloxyalkyl)-polysiloxane monomer and at least one additional hydrophilic monomer into a monomer mix and b) curing the monomer mix resulting from step a) to form a silicone-containing hydrogel composition.

2. A method for making a silicone-containing hydrogel composition comprising the steps of a) combining a ring-containing oxazolone monomer in the amount of from about 0.5 to about 10 weight percent able to be converted to a highly polar hydrophilic amino acid upon hydration with a bulky polysiloxanylalkyl (meth)acrylic monomer having the following formula:

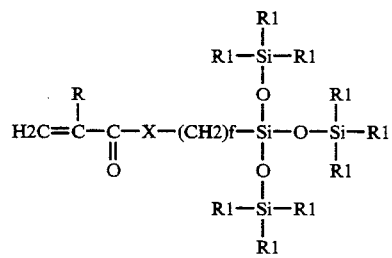

wherein:
X is O or NR;
each R is independently hydrogen or methyl; and
each $R_1$ is independently a lower alkyl or phenyl group; and
f is 1 or 3 to 10;
and at least one additional hydrophilic monomer into a monomer mix and b) curing the monomer mix resulting from step a) to form a silicone-containing hydrogel composition.

3. The method of claim 2 wherein said bulky polysiloxanylalkyl (meth)acrylic monomer is selected from the group consisting of methacryloxypropyl tris(trimethylsiloxy)silane, pentamethyldisiloxanylmethylmethacrylate, tris(trimethylsiloxy)methacryloxy propylsilane, phenyltetramethyldisiloxanylethyl acetate, and methyldi(trimethylsiloxy)methacryloxymethyl silane.

4. A method for making a silicone-containing hydrogel composition comprising the steps of a) combining a ring-containing oxazolone monomer in the amount of from about 0.5 to about 10 weight percent able to be converted to a highly polar hydrophilic amino acid upon hydration with a urethane-containing prepolymer and at least one additional hydrophilic monomer into a monomer mix and b) curing the monomer mix resulting from step a) to form a silicone-containing hydrogel composition.

5. The method of claim 4 wherein said silicone-containing prepolymer is a urethane-containing prepolymer having the following schematic representations:

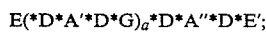

or

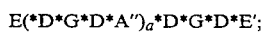

where
D denotes an alkyl diradical, an alkyl cycloalkyl diradical, a cycloalkyl diradical, an aryl diradical or an alkylaryl diradical having 6 to 30 carbon atoms;
G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;
*denotes a urethane or ureido linkage;
a is at least 1;
A″ denotes a divalent polymeric radical of formula:

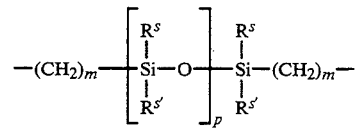

wherein:
$R^s$ and $R^{s'}$ independently denote an alkyl or fluoro-substituted alkyl group having 1 to 10 carbon atoms which may contain ether linkages between carbon atoms;
m is at least 1; and
p provides a moiety weight of 400 to 10,000;
E and E′ independently denote a polymerizable unsaturated organic radical represented by the formula:

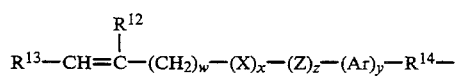

wherein:
$R^{14}$ denotes a divalent alkylene radical having 1 to 10 carbon atoms;
$R^{12}$ denotes H or $CH_3$;
$R^{13}$ denotes H, a ($C_1$-$C_6$) alkyl radical or a —CO—Y—$R^{15}$ group wherein Y is —O—, —S— or —NH— and $R^{15}$ is a alkyl radical having 1 to 12 carbon atoms;
X is —CO— or —OCO—;
Z is —O— or —NH—;
Ar denotes an aromatic radical having 6 to 30 carbon atoms;
w is 0 to 6;
x is 0 or 1;
y is 0 or 1; and
z is 0 or 1.

6. The method of claim 5 wherein said urethane-containing prepolymer is represented by the formula:

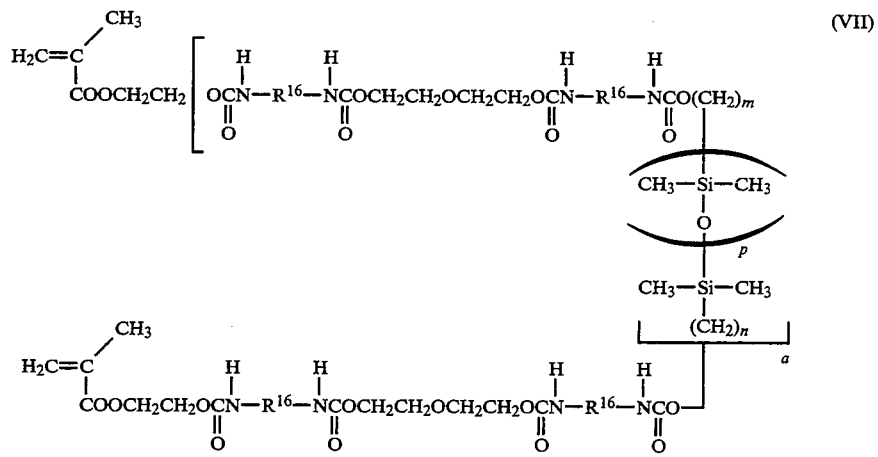

(VII)

wherein:

$R^{16}$ is a diradical of a diisocyanate after removal of the isocyanate group, and is most preferably the diradical of isophorone diisocyanate, and m, p and a are the same as previously defined.

7. The method of claims 1, 2 or 4 wherein said ring-containing oxazolone monomer is selected from the group consisting of 2-vinyl-4,4-dimethyl-2-oxazolin-5-one, 2-isopropenyl-4,4-dimethyl-2-oxazolin-5-one, cyclohexane-spiro-4'-(2'-isopropenyl-2'-oxazol-5'-one), cyclohexane-spiro-4'-(2'-vinyl-2'-oxazol-5'-one) and 2-(1-propenyl)-4,4-dimethyl-oxazol-5-one.

8. The method of claim 1, 2 or 4 wherein said ring-containing oxazolone monomer is 2-vinyl-4,4-dimethyl-2-oxazolin-5-one.

9. The method of claims 1, 2, or 4 wherein said additional hydrophilic monomer is selected from the group consisting of N,N-dimethylacrylamide and N-vinyl pyrrolidone.

10. A silicone-containing hydrogel composition prepared by polymerizing a monomer mix comprising 0.5 to 10 weight percent of a ring-containing oxazolone monomer able to be converted to a highly polar hydrophilic amino acid upon hydration, with an α, ω-bis(methacryloxyalkyl)polysiloxane monomer, and at least one additional hydrophilic monomer.

11. A silicone-containing hydrogel composition prepared by polymerizing a monomer mix comprising from about 0.5 to about 10 weight percent of a ring-containing oxazolone monomer able to be converted to a highly polar hydrophilic amino acid upon hydration with a bulky polysiloxanylalkyl (meth)acrylic monomer having the following formula:

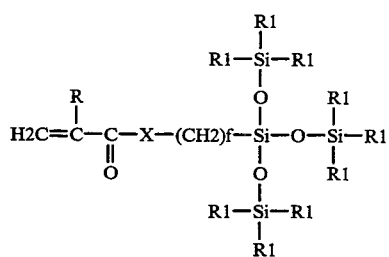

wherein:

X is O or NR;

each R is independently hydrogen or methyl; and each $R_1$ is independently a lower alkyl or phenyl group; and f is 1 or 3 to 10; and at least one additional hydrophilic monomer into a monomer mix and b) curing the monomer mix resulting from step a) to form a silicone-containing hydrogel composition.

12. The composition of claim 11 wherein said bulky polysiloxanylalkyl (meth)acrylic monomer is selected from the group consisting of methacryloxypropyl tris(-trimethylsiloxy)silane, pentamethyldisiloxanylmethylmethacrylate, tris(trimethylsiloxy)methacryloxy propylsilane, phenyltetramethyldisiloxanylethyl acetate, and methyldi(trimethylsiloxy)methacryloxymethyl silane.

13. A silicone-containing hydrogel composition prepared by polymerizing a monomer mix comprising from about 0.5 to about 10 weight percent of a ring-containing oxazolone monomer able to be converted to a highly polar hydrophilic amino acid upon hydration with a urethane-containing prepolymer and at least one additional hydrophilic monomer into a monomer mix and b) curing the monomer mix resulting from step a) to form a silicone-containing hydrogel composition.

14. The composition of claim 13 wherein said silicone-containing prepolymer is urethane-containing prepolymer having the following schematic representations:

E(*D*A'''*D*G)$_a$*D*A'''*D*E';

or

E (*D*G*D*A'')$_a$*D*G*D*E';

where

D denotes an alkyl diradical, an alkyl cycloalkyl diradical, a cycloalkyl diradical, an aryl diradical or an alkylaryl diradical having 6 to 30 carbon atoms;

G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

*denotes a urethane or ureido linkage;

a is at least 1;

A'' denotes a divalent polymeric radical of formula:

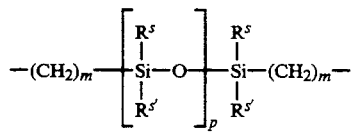

wherein:

$R^s$ and $R^{s'}$ independently denote an alkyl or fluoro-substituted alkyl group having 1 to 10 carbon atoms which may contain ether linkages between carbon atoms;

m is at least 1; and p provides a moiety weight of 400 to 10,000;

E and E' independently denote a polymerizable unsaturated organic radical represented by the formula:

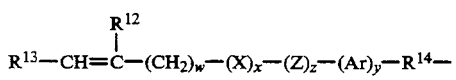

wherein $R^{14}$ denotes a divalent alkylene radical having 1 to 10 carbon atoms;

$R^{12}$ denotes H or $CH_3$;

$R^{13}$ denotes H, a ($C_1$–$C_6$) alkyl radical or a —CO—Y—$R^{15}$ group wherein Y is —O—, —S— or —NH— and $R^{15}$ is a alkyl radical having 1 to 12 carbon atoms;

X is —CO— or —OCO—;

Z is —O— or —NH—;

Ar denotes an aromatic radical having 6 to 30 carbon atoms;

w is 0 to 6;

x is 0 or 1;

y is 0 or 1; and z is 0 or 1.

15. The composition of claim 14 wherein said urethane-containing prepolymer is represented by the formula:

wherein:

$R^{16}$ is a diradical of a diisocyanate after removal of the isocyanate group, and is most preferably the diradical of isophorone diisocyanate, and m, p and a are the same as previously defined.

16. The composition of claims 10, 11 or 13 wherein said ring-containing oxazolone monomer is selected from the group consisting of 2-vinyl-4,4-dimethyl-2-oxazolin-5-one, 2-isopropenyl-4,4-dimethyl-2-oxazolin-5-one, cyclohexane-spiro-4'-(2'-isopropenyl-2'-oxazol-5'-one), cyclohexane-spiro-4'-(2'-vinyl-2'-oxazol-5'-one) and 2-(1-propenyl)-4,4-dimethyl-oxazol-5-one.

17. The composition of claims 10, 11 or 13 wherein said ring-containing oxazolone monomer is 2-vinyl-4,4-dimethyl-2-oxazolin-5-one.

18. The composition of claims 10, 11 or 13 wherein said additional hydrophilic monomer is selected from the group consisting of N,N-dimethylacrylamide and N-vinyl pyrrolidone.

19. A method for making a silicone-containing hydrogel composition comprising the steps of a) combining at least one hydrophilic (meth)acrylamido alkanoic acid monomer in the amount of from about 0.5 to about 10 weight percent with silicone-containing monomer and at least one hydrophilic monomer in addition to and different from said hydrophilic (meth)acrylamido alkanoic acid monomer into a monomer mix and b) curing the monomer mix resulting from step a) to form a silicone-containing hydrogel composition.

20. A silicone-containing hydrogel composition prepared by polymerizing a monomer mix comprising a hydrophilic (meth)acrylamido alkanoic acid, at least one silicone-containing monomer, and at least one hydrophilic monomer in addition to and different from said hydrophilic monomer.

21. An improved silicone-containing hydrogel formulation prepared by polymerizing a monomer mix comprising a silicone-containing monomer, and at least one hydrophilic monomer the improvement of which comprises the addition to said monomer mix of a hydrophilic ring-containing monomer able to be converted to a highly polar amino acid upon hydration in the amount of from about 0.5 to about 10 weight percent.

22. A contact lens made from the composition of claim 20.

23. A contact lens made from the composition of claims 10, 11 or 13.

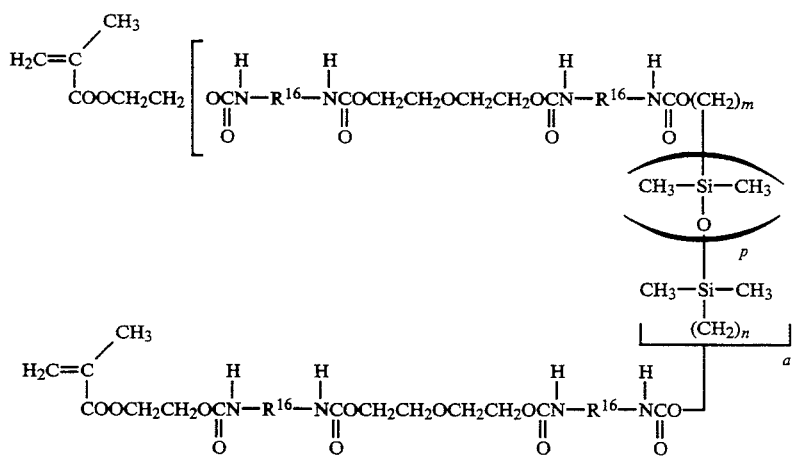

(VII)

* * * * *